United States Patent
Shell et al.

(10) Patent No.: US 7,601,369 B2
(45) Date of Patent: *Oct. 13, 2009

(54) COMPOSITION AND METHOD TO AUGMENT AND SUSTAIN NEUROTRANSMITTER PRODUCTION

(75) Inventors: William Shell, Los Angeles, CA (US); Elizabeth Charuvastra, Los Angeles, CA (US)

(73) Assignee: Targeted Medical Pharma Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/713,907

(22) Filed: Mar. 5, 2007

(65) Prior Publication Data

US 2007/0160690 A1    Jul. 12, 2007

Related U.S. Application Data

(62) Division of application No. 10/228,765, filed on Aug. 27, 2002.

(51) Int. Cl.
- *A61K 36/25* (2006.01)
- *A61K 36/258* (2006.01)
- *A61K 36/16* (2006.01)
- *A61K 36/54* (2006.01)
- *A61K 36/734* (2006.01)
- *A61K 31/221* (2006.01)
- *A61K 36/00* (2006.01)

(52) U.S. Cl. ............... 424/725; 424/728; 424/752; 424/739; 424/765

(58) Field of Classification Search ............ None
See application file for complete search history.

(56) References Cited

U.S. PATENT DOCUMENTS

| | | | | |
|---|---|---|---|---|
| 4,853,377 | A * | 8/1989 | Pollack | 514/161 |
| 5,215,750 | A * | 6/1993 | Keane, II | 424/440 |
| 6,291,533 | B1 * | 9/2001 | Fleischner | 514/682 |
| 6,340,482 | B1 * | 1/2002 | Jones | 424/736 |
| 6,399,089 | B1 * | 6/2002 | Yegorova et al. | 424/439 |
| 2002/0103139 | A1 * | 8/2002 | Weisspapir et al. | 514/26 |

* cited by examiner

*Primary Examiner*—Christopher R Tate
*Assistant Examiner*—Qiuwen Mi
(74) *Attorney, Agent, or Firm*—V. Craig Belair; Patton Boggs LLP

(57) ABSTRACT

This invention describes a method and composition to enhance the synthesis and release of the neurotransmitters by the oral administration of neurotransmitter precursors, along with natural plant substances that stimulate uptake of the neurotransmitters precursors, while adding natural plant substances that activate adenylate cyclase in order to avoid attenuation and prevent pharmacologic tolerance. The invention describes compositions for a medical foods that are designed to improve cognitive function, induced sleep, a improve Parasympathetic function, improve autonomic balance, increase nitric oxide production, reduce blood pressure, increase blood flow, and treat virus infections. The compositions include amino acids such as choline, herbs such ginkgo biloba, and other foods such as coca. The invention also describes the use of physiologic tests such as 24 hour ECG monitoring to create the appropriate combinations and assess the useful proportions.

4 Claims, 3 Drawing Sheets

COMPOSITION AND METHOD TO AUGMENT AND SUSTAIN NEUROTRANSMITTER PRODUCTION

CROSS-REFERENCE TO RELATED APPLICATIONS

This application is a divisional application of prior U.S. patent application Ser. No. 10/228,765, filed 27 Aug. 2002. The entirety of this aforementioned application is incorporated herein by reference.

FIELD OF THE INVENTION

This invention relates generally to medical foods and dietary supplements that augment neurotransmitter production by simultaneous administration of oral neurotransmitter precursors, a precursor uptake stimulator, a neurotransmitter releaser, a disinhibitor of the adenosine neuron brake, and an activator of adenylate cyclase to prevent tachyphylaxis.

PROBLEM

There has been increasing attention to the role that neurotransmitters and neuromodulators play in various aspects of health and disease. Neurotransmitters are the chemical messengers that allow one neuron to communicate with either a second neuron or an effector organ. The classic neurotransmitters are acetylcholine and norepinephrine that function within the autonomic nervous system. The autonomic nervous system, operating through its neurotransmitters, controls important body functions, such as heart rate, respiratory rate, gastrointestinal function, appetite, sleep, sexual performance, blood pressure and mood.

The increased scrutiny has lead to an appreciation of the effects that neurotransmitters and neuromodulators have on derangements of cognitive function, sleep disorders, mood, and memory. It is also known that neurotransmitters and neuromodulators play a crucial role in regulating the function of the cardiovascular, reproductive, musculoskeletal, immune, respiratory, and memory systems.

Numerous pharmaceutical agents have been developed which exert their effects by interfering with one or more neurotransmitter or neuromodulator systems. An important pharmaceutical mechanism is that of reuptake inhibition of neurotransmitters in the synaptic cleft of neuron junctions. The pharmaceuticals fluoxetine and fenfluramine are examples of neurotransmitter reuptake inhibitors.

All known neurotransmitters are synthesized within the neurons from their requisite precursor molecules. Thus, tryptophan becomes serotonin, choline becomes acetylcholine, tyrosine becomes epinephrine, and arginine becomes nitric oxide. The precursors are generally amino acids and are produced in the liver or are derived from the diet.

Importantly, administration of neurotransmitter and neuromodulator precursors has long been known to induce a physiologic response when initially administered. For example, administration of tryptophan—the precursor to the neurotransmitter serotonin, leads to the production of serotonin. Administration of choline leads to the production of acetylcholine.

Although, the administration of neurotransmitter precursors is known to acutely produce neurotransmitters, as evidenced by a physiologic response, the physiologic response induced by administration of a precursor to a neurotransmitter is often inconsistent, weak in magnitude, and rapidly attenuates so that the precursor administration is largely ineffective. The physiologic loss of neurotransmitter function often results in abnormal physiology and human disease. Accordingly, there is a need for an effective means for promoting the production of neurotransmitters and neuromodulators by administration of precursors, while avoiding the attenuation that frequently occurs with such precursor administration.

One approach to producing neurotransmitter and neuromodulators by the administration of precursors to the neurotransmitter was introduced by Wurtman and associates. They used tryptophan as a precursor to serotonin. Serotonin is known to reduce craving for carbohydrates. In Wurtman, et al, U.S. Pat. No. 4,210,637, a composition and method for selectively suppressing appetite for carbohydrates is described. The method includes administration of the serotonin precursor, tryptophan, along with a carbohydrate in order to suppress craving for carbohydrate.

Wurtman subsequently administered tryptophan to humans in doses up to 2300 mg per day for many days but did not find a consistent appetite suppression because many of the subjects experienced attenuation of the response secondary to tolerance. Wurtman, et al, in U.S. Pat. No. 4,309,445, abandoned the use of precursor administration to increase serotonin production and described a method that focused on the use of a serotonin reuptake inhibitor, d-fenfluramine, to increase brain levels of serotonin, thereby reducing craving for carbohydrates. The d-fenfluramine and a related molecule, fenfluramine, were subsequently administered to several million humans, a practice discontinued because the re-uptake inhibition caused side effects, including heart valve lesions and pulmonary hypertension.

In U.S. Pat. No. 4,687,763, Wurtman, et al, disclosed that tryptophan feeding in conjunction with melatonin can acutely increase brain serotonin concentration and reduce carbohydrate craving. They did not examine attenuation or tolerance in this disclosure. They did disclose, however, that on initial administration of tryptophan, serotonin concentration in the brain creases.

In Pollack U.S. Pat. No. 4,650,789, a method and composition for increasing production of serotonin is described. The method requires that tryptophan be concomitantly administered with acetylsalicylic acid. They only disclosed acute administration of the precursor and did not disclose either the tolerance or attenuation of precursor administration. They did not suggest a solution for the attenuation problem In 1992, Weintraub observed that phentermine and fenfluramine when used together induced weight loss, reduced appetite and reduced carbohydrate craving in humans. The results of using phentermine and fenfluramine were attributed to their separate effects on serotonin and dopamine. Weight loss could be obtained for approximately 3 months, but the effects attenuated, and a weight plateau was reached. The patients could only sustain their initial weight loss, but not lose additional weight by maintaining the use of the drugs, or actually increasing the dose of the drugs. The phentermine/fenfluramine combination had induced a physiologic tolerance. If the patients discontinued the drugs, rebound weight gain occurred, frequently returning the patients to their original weight. In many patients, super-rebound occurred inducing a weight gain that exceeded the original weight loss. Thus, the initial physiologic tolerance caused a deleterious side effect of rebound and super-rebound,.

In Wurtman, et al, U.S. Pat. No. 5,118,670, a composition and method for increasing brain dopamine is described. The effects described are acute effects. The combination is not administered for sufficient duration to assess attenuation and tolerance. Similarly, in Wurtman, et al, Pat. No. 4,673,689, a method is disclosed for the use of tyrosine to potentiate sympathomimetic agents such as phenylpropanolamine, ephedrine, and pseudoephedrine. The effects described are acute and tolerance is not assessed. The combination of tyrosine with the sympathomimetic agents has not been commercially applied, suggesting that attenuation is an important factor. Such tolerance to sympathomimetic agents is a well known effect of the use of sympathomimetic agents. Tolerance is described in the standard texts of pharmacology, where loss of response after successive administration of sympathomimetic agents is used to teach the general principals of physiologic tolerance and dependence.

Wurtman (U.S. Pat. No. 4,636,494) disclosed the administration of choline co-administered with a drug to augment brain production of acetylcholine. They showed inconsistent results with an approximately 50% response rate. They administered the choline for two weeks and did not document attenuation.

Delgado, et al demonstrated that ingestion of tryptophan free diets in patients with depression results in a rapid decline of blood plasma concentrations of tryptophan. The reduction of blood tryptophan resulted in rapid onset of symptoms of depression.

Richardson (U.S. Pat. No. 5,919,823) using the administration of large neutral amino acids found that movement disorders secondary to drugs could be treated but that the response is often inconsistent and improvement was only seen in approximately 50% of patients and for short periods.

Hinz (U.S. Pat. No. 6,403,657) disclosed the simultaneous administration of a serotonin reuptake inhibitor with a monoamine oxidase inhibitor along with supplementation with 5-hydroxytryptophan and tyrosine to ameliorate the plateau phase of weight loss. They disclosed the use of Citalopram and phentermine with tyrosine. In U.S. Pat. No. 6,384,008, Hinz disclosed the use of phentermine and Citalopram with both tyrosine and 5-hydroxytryptophan.

These observations all indicate that administration of a neurotransmitter precursor results in production of the associated neurotransmitter. The production of the neurotransmitter results in a physiologic response. The response to the precursor is short-lived and inconsistent. Administration of precursor to neurotransmitters may ameliorate some aspects of tachyphylaxis.

These observations indicate that there is a need for improved methods to stimulate neurotransmitter production. These methods should lead to augmented and sustained response while avoiding tachyphylaxis to precursor administration.

The pharmacology literature has long recognized the existence of tolerance and attenuation, also termed tachyphylaxis. The effect is particularly prominent in psychotropic agents including amphetamines, analgesics, antidepressants, antianxiety agents, and psycho stimulants such as cocaine. The mechanisms related to tolerance are obscure but are thought to be related to upregulation of receptors and upregulation of enzyme systems related to first messenger receptor systems. Despite extensive study, avoidance of tolerance has been an elusive goal.

For example, attenuation to nitroglycerin has been particularly well studied. Continuous administration of nitroglycerin by either oral or transcutaneous routes leads to both attenuation and complete tolerance to nitroglycerin. The attenuation occurs over 7 to 10 days of administration. Withdrawal of the agents leads to a nitrate withdrawal syndrome. Despite extensive study, avoidance of nitrate tolerance has not been achieved. The effects of nitroglycerin are related to nitric oxide metabolism.

Shell has observed in studies dating to 1987 that the initial effects of formulations containing neurotransmitter precursors rapidly attenuate. Appetite suppression from tyrosine acutely occurs but is lost in approximately 7 days. Choline administered in combination with xanthines induces heart rate reduction and altered heart rate variability but the combination attenuated in approximately 7 days. These observations are consistent with the known effects of xanthines, which show attenuation within 7 days of administration. Caffeine attenuation effects are also well known, particularly the alteration of heart rate and leads to coffee withdrawal syndromes. The attenuation of theophylline in the treatment of asthma is well documented, leading to its reduced use in the treatment of asthma.

Administration of amino acid precursors to stimulate neurotransmitter activity depends on an active uptake of the amino acid into the neuron, synthesis of the neurotransmitter and release of the neurotransmitter by the neuron. Agents that can increase uptake of amino acids into neurons synthesis into include plant substances that contain flavanoids (Fitzpatrick), herbs such as ginkgo biloba, spices such as cinnamon, certain amino acids such as glutamine and histidine, xanthines such as caffeine and certain vitamins. Ginkgo biloba for example is known to increase the synthesis of acetyl choline from choline by increasing the uptake of choline. Cinnamon is known to increase the uptake of arginine to enhance the synthesis of nitric oxide. Caffeine is known to increase the production of norepinephrine from tyrosine.

Agents that are known to cause release of neurotransmitters from neurons include the stimulatory amino acids glutamate and aspartate. In addition, agents that can stimulate release of neurotransmitters include both the xanthines and the sympatheticomimetic agents. The xanthines include theobromine and caffeine. The sympatheticomimetic agents include ephedrine.

Many cell, particularly neurons, are inhibited from activity by active cell mechanisms. The receptors that control the active inhibition of neurons are the purinoreceptors. These receptors respond to adenosine containing molecules including ATP, ADP, AMP, and adenosine. This inhibitory effect of adenine containing molecules on neuron function has been termed the adenosine brake. In neurons, the adenosine brake acts to inhibit a neuron from firing. Thus, provision of an amino acid precursor such as tyrosine, to a non-firing neuron will result in no response, the tyrosine will be cleared from the blood, and no physiologic effect will be noted. Thus, to enhance the effectiveness of amino acid precursors to the neurotransmitters, a means must be found to relieve the adenosine brake. Inhibitors of the adenosine brake include the xanthines. Caffeine is an especially potent inhibitor of the adenosine brake. For example, Dullo, et al., demonstrated that in brown adipose tissue caffeine increased fat cell oxygen consumption and the increase is directly related to the ability of caffeine to relieve the adenosine brake.

Attenuation and tolerance limit the utility of administration of amino acid precursors to the neurotransmitters. Tolerance is particularly prevalent in the sympatheticomimetic agents—those that stimulate cyclic AMP production by activation of adenyl cyclase. These agents stimulate cyclic AMP and appear to down regulate the number of receptor molecules to account for the observed attenuation and tolerance. Activators of adenyl cyclase that do not down regulate the adenyl cyclase receptors could have potential utility in avoiding attenuation and tolerance. A class of agents that stimulates adenyl cyclase without attenuation includes the herbs Hawthorn Berry and Willow Bark. Hawthorn Berry can be used for many months to stimulate heart contractility without attenuation while activating adenyl cyclase. The use of Hawthorn Berry with amino acid precursors to stimulate neurotransmitters without attenuation has not been used prior to our invention.

Xanthines are a class of agents that have similar but not identical effects. The xanthines include ephedrine, caffeine, and theobromine. The potency of the xanthines has generally been ranked according to the ephedrine, caffeine, and theobromine series. The effects of the individual xanthines are not identical. Caffeine is a potent stimulant to uptake and release of amino acids while ephedrine is a potent stimulant to heart rate. Moreover, the xanthines are often used in combination with sympatheticomimetic agents—ephedrine with caffeine is a frequent combination.

A large number of dietary supplements and medical foods have used various combination of these mechanism with variable effects. For example, ephedrine and caffeine have been combined. Tyrosine, ephedrine, and caffeine have been combined in various proportions. Choline and ginkgo biloba have been combined. The combination of a precursor, stimulant to uptake/release, inhibition of the adenosine brake, and non-attenuating activation of adenyl cyclase has not been utilized prior to this invention.

In experiments dating to 1987, the inventors have worked on combinations of these mechanisms that have produced results that are both synergistic and surprising. The results indicate that the combination of the five elements lead to a result that is more then the individual agents acting alone. The effects are sustained and do not attenuate.

The methods used to assess the production of neurotransmitters include various tests of physiologic function. The tests include but are not limited to test of heart rate, tests of heart rate variability, tests of cardiac repolarization, tests of body temperature, tests of symptoms reflecting autonomic nervous system function and tests of blood flow. Neurotransmitter synthesis, release, and reuptake provide the chemical messengers used to control the autonomic nervous system. Therefore, physiologic tests of autonomic function reflect the production of neurotransmitters.

For example, it is long known that heart rate is under the control of the autonomic nervous system. The human autonomic nervous system controls the heart rate on a beat to beat basis to control the amount of blood ejected by the heart. The balance between the sympathetic and parasympathetic components of the autonomic nervous system will determine the cycle length of heart beat. Beat-to-beat heart rates and average heart rates are controlled by the autonomic nervous systems. The heart rate and changes in heart rate can be used to assess the status of neurotransmitter production.

A more sophisticated measurement of autonomic nervous system control of heart rate is termed heart rate variability (HRV) analysis. In this method at least five minutes of heart rate data is accumulated. The data is then analyzed in either the time domain or the frequency domain. In the time domain, each successive beat is calculated as an RR-interval in msec. A series of statistics are calculated including means and variances to reflect the autonomic control of heart rate.

In the frequency domain methods, the successive RR-intervals are converted to frequency using Fast Fourier Transform or similar methods. Using the derived frequencies several bands are identified including the very low frequency (VLF), the low frequency (LF), and the high frequency (HF). The sum of all the bands is termed the total power. The area of the HF band has been identified with parasympathetic autonomic nervous system function. The LF/HF ratio is identified with Sympathetic/parasympathetic balance. There is no specific marker yet identified that is specific for sympathetic autonomic nervous system function. The total power is a measure of the total activity of the autonomic nervous system—reduced total power reflects suppression of autonomic nervous system activity.

Another measure of autonomic nervous system activity is a measurement of the QTc-interval on the electrocardiogram. Prolongation of the QTc-interval is a reflection of enhanced sympathetic activity.

The assessment by physiologic tests such as change in heart rate, change in heart rate variability, change in the QTc-interval, change in body temperature, and change in symptoms reflective of autonomic function can be used to measure the activity of the autonomic nervous system and thus a measure of neurotransmitter production.

Accordingly, this invention describes a method to stimulate augmented neurotransmitter synthesis, providing sustained neurotransmitter activity, while avoiding attenuation of precursor administration.

Solution

This invention has the object of achieving increased production of specific neurotransmitters, as indicated by a physiologic response, by not only providing neurotransmitter precursors but also stimulants to precursor uptake, release of a neuronal inhibiting brake, stimulants to neurotransmitter release, and components to avoid the attenuation previously associated with oral administration of neurotransmitter precursors. This invention has the advantage of allowing a synergistic effect of the components reflected by augmented responses, sustained effect of administration of neurotransmitter precursors over time, and avoiding development of pharmacologic tolerance.

This invention also provides methods and compositions for formulations of medical foods and dietary supplements that increase the activity of specific neurotransmitters and neuromodulators. This invention is based upon the discovery that certain neurotransmitter precursors will act synergistically with certain naturally occurring plant sources, particularly other amino acids, herbs and spices, in promoting synthesis and release of the selected neurotransmitter. In particular, precursors for the neurotransmitters acetylcholine, GABA, glutamate, serotonin, and nitric oxide are orally administered with one or more plant or animal substances, particularly glutamate, ginkgo biloba, hawthorn berry, cinnamon, or caffeine to enhance neurotransmitter and neuromodulator production and activity. When administered alone, these neurotransmitter precursors are poorly effective and rapidly lose any effect. When administered in inappropriate combinations, the administration of the combinations has no effectiveness, or rapidly undergoes pharmacologic tolerance.

This invention describes a method for defining the range of appropriate combinations and concentrations to achieve neurotransmitter production, while avoiding tachyphylaxis. Increased neurotransmitter production is reflected in a physiologic response. The inventors have used physiologic testing to define the appropriate combination of precursor and plant sources, while also allowing the definition of the range of doses that create the desired effect without attenuation. The testing methods include the assessment of heart rate, heart repolarization measurements, blood pressure, body temperature, sexual responsiveness, appetite and other measures of autonomic function to assess which combinations and dose ranges are effective, and to assess the potential for attenuation.

The combinations of neurotransmitter precursors with other animal and plant components provide surprisingly synergistic effects when assessed by specific measurements of physiologic responses. For example, the use of choline and hawthorn berry to elicit acetylcholine effects, in the concentrations described in this invention, result in unexpected avoidance of attenuation of heart rate variability that could not be predicted without the availability of specific physiologic assessment tests of acetylcholine effects.

SUMMARY

This invention describes a method and compositions to enhance the production of neurotransmitters by the oral administration of neurotransmitter precursors, along with natural plant and animal substances that stimulate uptake of the neurotransmitter precursors, cause release of neurotransmitters, cause disinhibition of the neuronal brake, and activate adenylate cyclase in order to avoid tachyphylaxis and prevent pharmacologic tolerance. The invention describes compositions for medical foods and dietary supplements that are designed to improve cognitive function, induce sleep, improve parasympathetic nervous system function, improve autonomic nervous system balance, increase nitric oxide production, reduce appetite, reduce blood pressure, increase blood flow, and reduce the duration of virus infections. The compositions include amino acids such as choline, herbs such ginkgo biloba, and other foods such as cocoa. The invention also describes the use of physiologic tests of autonomic nervous system function that used to create the appropriate combinations and to assess the effective proportions.

DETAILED DESCRIPTION OF THE DRAWINGS

The following descriptions illustrate the manner in which the principles of the invention are applied, but they are not to be construed as limiting the scope of the invention.

Figure 1:
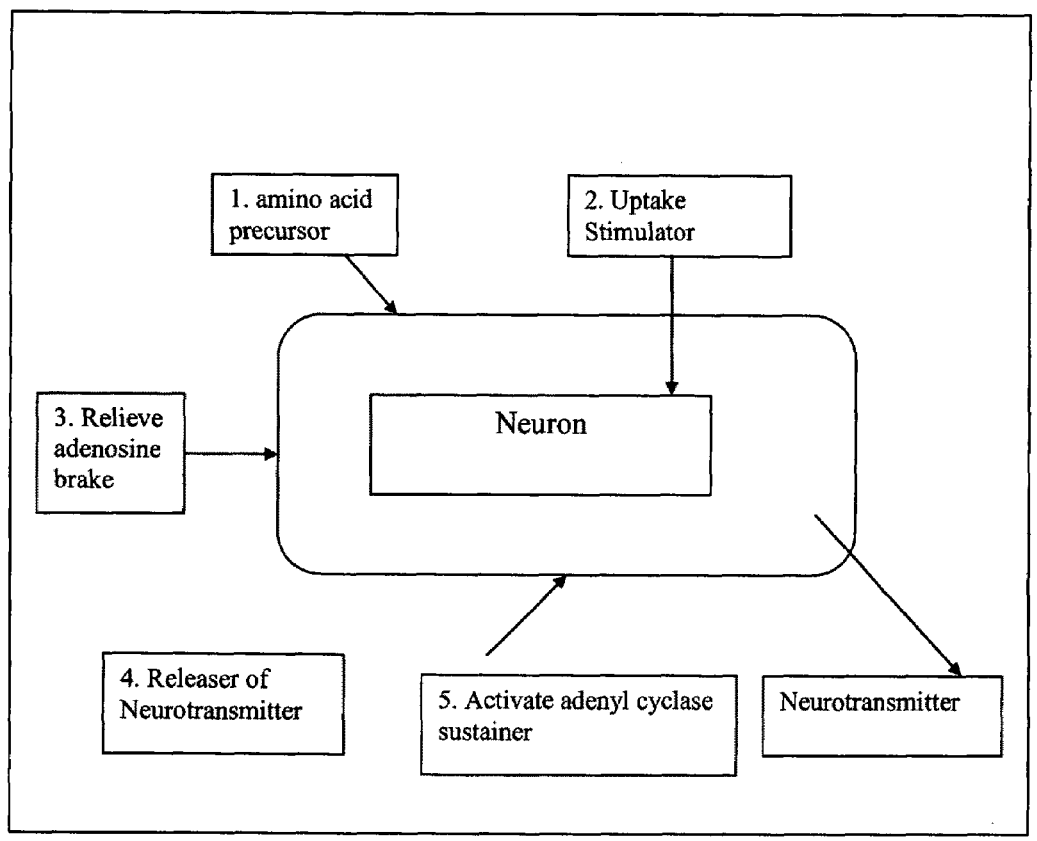
FIG. 1 illustrates a block diagram of an exemplary five elements according to an embodiment of the present invention.

Choline, glutamic acid, tryptophan, 5-hydroxytryptophan, arginine, and glutamine form a class of precursors for neurotransmitters that are active in the nervous system and effector organs. In this invention, one or more precursors to neurotransmitters (Element #1 Precursor) are administered in combination with a uptake stimulator such as ginkgo biloba, to promote uptake of the precursor (Element #2 Uptake Stimulator). The combination includes an element, such as a xanthine, to disinhibit the neuron adenosine brake (Element #3 Disinhibitor). The combination also includes another element such as ginseng, or an amino acid, such as glutamate (Element #4 Releaser) that functions to promote the release of the selected neurotransmitter. Finally, this initial combination is enhanced by further addition of a substance (Anti-attenuator Element #5), such as hawthorn berry, selected to stimulate adenylate cyclase in order to avoid attenuation of neurotransmitter production (FIG. 1).

Thus, there are five elements to this invention, including a precursor to a selected neurotransmitter, a second component to enhance uptake of the precursor, a third component to disinhibit the neuron, a fourth component to simulate release of the neurotransmitter and a fifth element to avoid attenuation. The choice of the individual five components and their relative proportions is governed by the use of a physiologic test that is designed to measure the effect of the selected neurotransmitter on autonomic nervous system function. Surprisingly, one skilled in the art could not predict either the combinations or the proportions of the ingredients, without the use of the physiologic test.

It is important that the five elements be administered simultaneously and in the correct proportions. If one of the elements is eliminated, the physiologic effect does not occur. If the proportions are not correct, either the physiologic effects do not occur or an unexpected physiologic, even deleterious, effect can occur.

It is important to choose the precursor correctly. The choice of the precursor determines the neurotransmitter that is synthesized, and the subsequent physiologic effect produced. The choice of choline will lead to acetylcholine production, which results in a reduced heart rate when the correct elements and proportions are administered. The choice of tryptophan or 5-hydroxytryptophan results in production of serotonin, thereby reducing appetite or inducing sleep. The choice of arginine results in the production of nitric oxide, increasing vasodilation and increased skin temperature. The choice of the precursor defines the specificity of the response.

The precursors can be combined to elicit more then one physiologic response as long as the precursors do not compete for the same receptor sites. Choline can be combined with 5-hydroxytryptophan to elicit both acetylcholine and serotonin responses. Choline and arginine can be combined to elicit both acetylcholine and nitric oxide response.

The choice of the herb or other natural source that can stimulate uptake of the precursor can be selected from a number of herbs or other sources including but not limited to ginkgo biloba, which can stimulate the uptake of choline, or cinnamon, which can stimulate the uptake of arginine.

The component that stimulates release of neurotransmitters can be selected from a variety of herbs, natural sources, and pharmaceuticals. Ginseng and St. Johns Wort can release neurotransmitters. Glutamic acid and glutamine become glutamate that acts as a neuroexcitatory agent by causing neurotransmitter release. Glutamate is a strong neuroexcitatory amino acid that causes release of neurotransmitters.

The components that cause the disinhibition of the neuronal brake can be selected from the class of xanthines or sympatheticomimetic. The xanthines that can be chosen include theobromine, caffeine, and theophylline. The sympatheticomimetic include ephedrine, pseudoephedrine, and synephrine.

The component designed to avoid attenuation by activating adenylate cyclase can be selected from herbs, plant sources, or pharmaceuticals. The herbs can include hawthorn berry. Plant sources can include glycosides. Pharmaceuticals can include caffeine or ephedrine.

An embodiment of the invention is a combination of the five elements that is specifically designed to enhance the function of the parasympathetic component of the autonomic nervous system, by stimulating the synthesis and release of acetylcholine. The physiologic endpoint is a lowering of heart rate and blood pressure. The combination of elements includes choline, coca, gingko biloba, glutamic acid, and hawthorn berry. The choline is administered in a range of 20-100 mg. The ginkgo biloba is administered in a range of 50-100 mg. The glutamic acid is administered in a range of 20-100 mg. The hawthorn berry is administered in a range of 20-40 mg. Cocoa is used as a source of caffeine and theobromine, and is administered in a range of 100-200 mg. If these relative proportions are not maintained, the enhancement of parasympathetic function is either not obtained, or undergoes rapid attenuation. The physiologic effect can be measured by tests that include but are not .limited to, measurements of heart rate, heart rate variability, pulse rate, blood pressure, or respiratory rate.

Another embodiment of the invention is a combination of elements designed to augment both serotonin and acetyl choline release. The physiologic endpoint is the induction of sleep and maintenance of deep sleep. The induction of deep delta sleep is activated by brain parasympathetic nervous system activity. The combination of components of the embodiment includes a serotonin precursor, choline or other choline substrate, gingko biloba, coca, glutamic acid, and hawthorn berry. The serotonin precursor can be either tryptophan or 5-hydroxytryptophan, which are administered respectively, in the range of 20-100 mg. The choline is administered in a range of 20-100 mg. The ginkgo biloba is administered in a range of 50-100 mg. The glutamic acid is given in a range of 20-100 mg. The hawthorn berry is given in a range of 20-40 mg. Cocoa is used as a source of caffeine and theobromine in a range of 100-200 mg. If the relative proportions are not maintained, adequate serotonin production does not occur. Without the hawthorn berry or a similar component, the induction of sleep activated by precursor administration undergoes rapid attenuation. The attenuation occurs within days. The physiologic effect is measured by assessing induction of sleep, measurement of sleep stages, defining heart rate variability, heart rate, and/or analysis of circadian rhythms of autonomic nervous system function.

A further embodiment of the invention is a combination designed to augment nitric oxide and acetylcholine. The physiologic endpoint is an increase in nitric oxide production, increase in heart rate, increase in body temperature, or fall in blood pressure. The combination of components includes arginine, choline, gingko biloba, glutamic acid, and hawthorn berry. Arginine is administered in the range of 20-100 mg. Choline is administered in a range of 20-100 mg. The ginkgo biloba is administered in a range of 50-100 mg. The glutamic acid is given in a range of 20-100 mg. The hawthorn berry is given in a range of 20-40 mg. Cocoa is used as a source of caffeine and theobromine in a range of 100-200 mg. If the relative proportions are not maintained, heart rate does not increase, body temperature increase, secondary to skin vasodilation, does not occur and pulmonary bronchodilation does not occur.

An additional embodiment of the invention is a combination designed to increase nitric oxide in white blood cells and to simultaneously increase the release of white blood cells in order to fight viral infections. The physiologic effect is the increase in white blood cell concentration and a reduction of the symptoms of the viral infection. The combination of components includes echinacea, arginine, choline, cocoa, gingko biloba, glutamic acid, and hawthorn berry. The echinacea is administered in the range of 50-100 mg. Arginine is administered in the range of 20-100 mg. Choline is administered in a range of 20-100 mg. The ginkgo biloba is administered in a range of 50-100 mg. The glutamic acid is administered in a range of 20-100 mg. The hawthorn berry is administered in a range of 20-40 mg. Cocoa is used as a source of caffeine and theobromine, and is administered in a range of 100-200 mg. If the relative proportions are not maintained, white blood cell count does not increase, heart rate does not increase, body temperature secondary to skin vasodilation does not occur and pulmonary bronchodilation does not occur.

An additional embodiment of the invention is a combination designed to increase norepinephrine, epinephrine, dopamine, histamine, serotonin and acetylcholine. The physiologic effect is the suppression of appetite, suppression of graving for carbohydrate, fat burning, and increased heart rate. The combination of components includes tyrosine, histidine, tryptophan, choline, gingko biloba, glutamic acid, and hawthorn berry. The tyrosine is administered in the range of 50-100 mg. Histidine is administered in the range of 20-100 mg. Choline is administered in a range of 20-100 mg. The ginkgo biloba is administered in a range of 50-150 mg. The glutamic acid is administered in a range of 20-100 mg. The hawthorn berry is administered in a range of 20-40 mg. Cocoa is used as a source of caffeine and theobromine, and is administered in a range of 100-200 mg. If the relative proportions are not maintained heart rate does not increase, appetite suppression does not occur, carbohydrate graving suppression dose not occur, body temperature increase secondary to increased metabolic rate does not occur and fat burning does not occur.

The combination of precursor, uptake stimulator, attenuation inhibitor, and releaser may be administered orally or intravenously. The combination and proportion must be maintained to insure the desired effect. The dosage form may be capsules, suspension caplets, chewable wafers, tablets, or powders.

A variety of testing methods that assess autonomic nervous system function or other aspects of neurotransmitter function can assay the effects of the combination of the elements. The effects can be measured by assessment of symptoms using questionnaires with quantitative scales, assessing the quality of sleep, cognitive ability, short-term memory, long-term memory, body temperature regulation, muscle pain, peripheral sensation, and fatigue. The effects can be quantified by objective measurements of autonomic nervous system function; measurements can include blood pressure, heart rate, heart rate variability, QT-interval analysis, respiratory rate, airway resistance, degree of peripheral vascular dilation, the diameter of peripheral arteries, degree of vascular engorgement, skin temperature, and peripheral vascular resistance. In addition, neurotransmitter concentration can be directly measured by techniques such as PET scanning, Spect scanning, cerebrospinal fluid concentrations and blood concentration of either the neurotransmitter or its metabolites.

In addition, a variety of testing can be used to assess appetite control, carbohydrate craving control, and fat burning. The tests include questionnaires, body weight, and percent of body weight as fat, serotonin blood concentrations, and body girth.

Acetylcholine deficiencies are involved in diseases such as Alzheimer's disease, diabetes mellitus, chronic fatigue syndrome, fibromyalgia, toxin induced organic brain disease, peripheral neuropathies, autonomic dysregulation, and senile cognitive disorders. Deficiencies of acetylcholine are related to memory disorders, muscle fatigue, and peripheral neuropathies. This invention has the advantage of correcting the acetylcholine deficiencies without pharmaceuticals and with components normally present in the diet.

Serotonin deficiencies are involved in diseases such as sleep disorders, anxiety disorders, panic disorders, depression, eating disorders, and chronic pain syndromes. This invention has the advantage of correcting the serotonin deficiencies without pharmaceuticals and with components normally found in the diet.

Nitric Oxide deficiencies are involved in diseases such as atherosclerosis, hypertension, pulmonary hypertension, sexual dysfunction, immune disorders, infectious disease, peripheral vascular disease, ischemic heart disease, asthma, disorders of bronchconstriction, and diabetes mellitus. This invention has the advantage of correcting the nitric oxide deficiencies without pharmaceuticals and with components normally found in the diet.

Tyrosine deficiencies are involved in disorders of appetite control, mood disorders, and Parkinson's disease.

Glutamate and GABA deficiencies are involved in memory disorders, addictions, anxiety disorders, and depression. This invention has the advantage of correcting the glutamate deficiencies without pharmaceuticals and with components normally found in the diet.

Combinations of neurotransmitter precursors can be used to target more then one neurotransmitter deficiencies. For example, the effects of acetylcholine and nitric oxide can be targeted simultaneously. One of the novel aspects of this invention is to simultaneously target two or more neurotransmitter deficiencies, using physiologic testing to formulate both the effective combinations and the relative proportions.

The following examples illustrate formulations that produce the desired physiologic effect. All of the following examples derive their effects from the synergistic actions of the individual components.

EXAMPLE 1

A useful formulation to produce acetylcholine and glutamate is choline 600 mg, acetylcamitine 100 mg, glutamate 100 mg, ginkgo biloba 50 mg, hawthorn berry 50 mg, cocoa 400 mg, and dextrose 200 mg. A preferred dosage is two capsules in the morning and two capsules at bedtime. The formulation is designed to reduce heart rate and increase the parasympathetic component controlling heart rate. Other dosage schedules can be used depending on the results of subsequent symptoms and the results of objective physiologic tests.

EXAMPLE 2

A useful formulation to produce acetylcholine and serotonin is choline 600 mg, acetylcamitine 20 mg, 5-hydroxytryptophan 50 mg, ginkgo biloba 50 mg, glutamate 100 mg, cocoa 400 mg and dextrose 200 mg. The formulation is designed to induce sleep. A preferred dose to induce sleep is two capsules at bedtime. Other dosage schedules to induce other desirable effects of serotonin such as appetite control and amelioration of depression can be used.

EXAMPLE 3

A useful formulation to produce nitric oxide and acetylcholine is arginine 125 mg, choline 125 mg, glutamine 25 mg, ginkgo biloba 50 mg, hawthorn berry 25 mg, cocoa 67.5 mg, cinnamon 50 mg, histidine 12.5, caffeine 6.25 mg and dextrose 67.5 mg. A preferred dosage is two capsules, twice daily. Other dosage schedules can be used depending on the results of subsequent symptoms and the results of objective physiologic tests.

EXAMPLE 4

Figure 2:
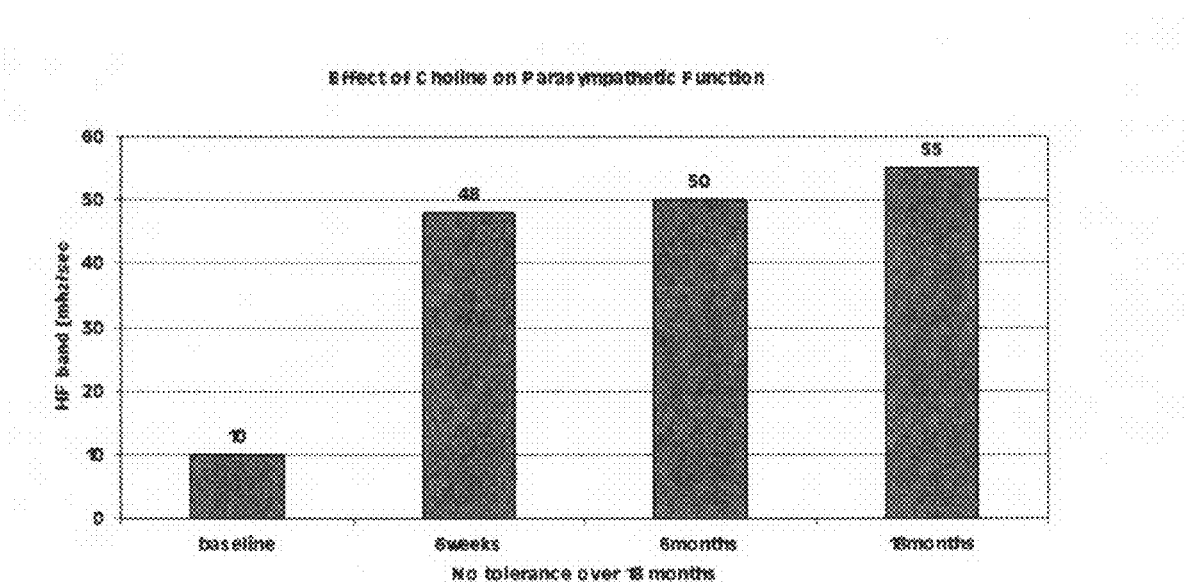
FIG. 2 illustrates a graph depicting the effect of choline on parasympathetic function according to an embodiment of the present invention.

This example illustrates the use of an acetylcholine and glutamate combination for the treatment of diabetic neuropathy. Diabetics develop abnormalities of central and cranial nerves. The peripheral neuropathy leads to sensory dysfunction, physical trauma, leading to loss of limb. The central neuropathy, particularly dysfunction of the vagal and glossopharyngeal nerves, leads to autonomic nervous system dysfunction. Among the methods to assess autonomic nervous system dysfunction is heart rate variability measured from 24-hour ambulatory ECG recording, particularly the HF band reflecting parasympathetic autonomic nervous system activity. A 58-year-old diabetic male had peripheral neuropathy, manifested both as decreased sensation in the legs and as autonomic dysfunction; the autonomic dysfunction could be measured as decreased parasympathetic nervous system activity as defined on 24 hour ECG recording of the RR-interval (heart rate variability). He took the acetylcholine/glutamate preparation described in example 1. He took two capsules in the morning and two capsules before bedtime. After six weeks, the peripheral neuropathy disappeared and sensation in his legs returned. Initially, his parasympathetic nervous system function, measured as the high frequency component of the Fast Fourier Transform of the RR-interval frequency distribution (HF-band), was 10 mhz/sec2. Following the 6-week trial of the acetylcholine/glutamate preparation, the parasympathetic function HF-band increased to 48, a normal value. The improvement was maintained for 6-months. At 6-months, the HF-band was 50. At 18 months, the HF band was 55 indicating no attenuation or tolerance effect (FIG. 2).

EXAMPLE 5

This example illustrates the combined use of both the preparation for acetylcholine/glutamate (example 1) and the preparation for acetylcholine/serotonin (example 2) for the treatment of subjects exposed to toxic chemicals. Subjects exposed to a variety of toxic chemicals experience sleep disorders, temperature dysregulation, peripheral neuropathy, and other signs of autonomic nervous system dysfunction. A 54 your old male was exposed to nitrogen tetroxide after an explosion of a railroad tanker car. He experienced severe autonomic nervous system dysfunction that was measured from 24 hour ECG recording. He displayed a reduction of his HF band parasympathetic band), reduced circadian activation of parasympathetic nervous system function at night, and increase of his QTc interval, another measurement of autonomic nervous system balance. He took three capsules of the acetylcholine/serotonin preparation at bedtime along with two capsules of the acetylcholine/glutamate preparation in the morning. Within two weeks, his symptoms improved. After 6-weeks, his HF band returned to normal, he activated his parasympathetic circadian rhythms at night and his QTc interval normalized. He was retested at the end of three months; he had maintained the improvement in his parasympathetic nervous system function and the reduction in his QTc interval, indicating avoidance of tolerance. His clinical symptoms remained improved during this time. He has continued his treatment for two years with continued suppression of symptoms. If treatment is stopped for as little as 10 days, his symptoms recur.

EXAMPLE 6

A 54-year-old male with hypertension took a preparation designed to increase nitric oxide and acetylcholine (example 3). The preparation included choline, arginine, hawthorn berry, cocoa, dextrose, and cinnamon. The baseline blood pressure was 170/105 mm Hg. the blood pressure was measured every five minutes for 120 minutes. The blood pressure fell to 130/85 mm Hg in fifteen minutes and remained reduced for the remaining 105 minutes. By the next morning, the blood pressure had returned to 170/100 mm Hg. Ingestion of hawthorn berry alone resulted in no change in the blood pressure over the next 120 minutes. The subject took the preparation twice daily for six weeks. At the end of the six-week time, the process was repeated. At day one, the morning blood pressure was 170/105 and fell to 130/85 after fifteen minutes. The next day, ingestion of hawthorn berry alone showed no result.

EXAMPLE 7

Figure 3:
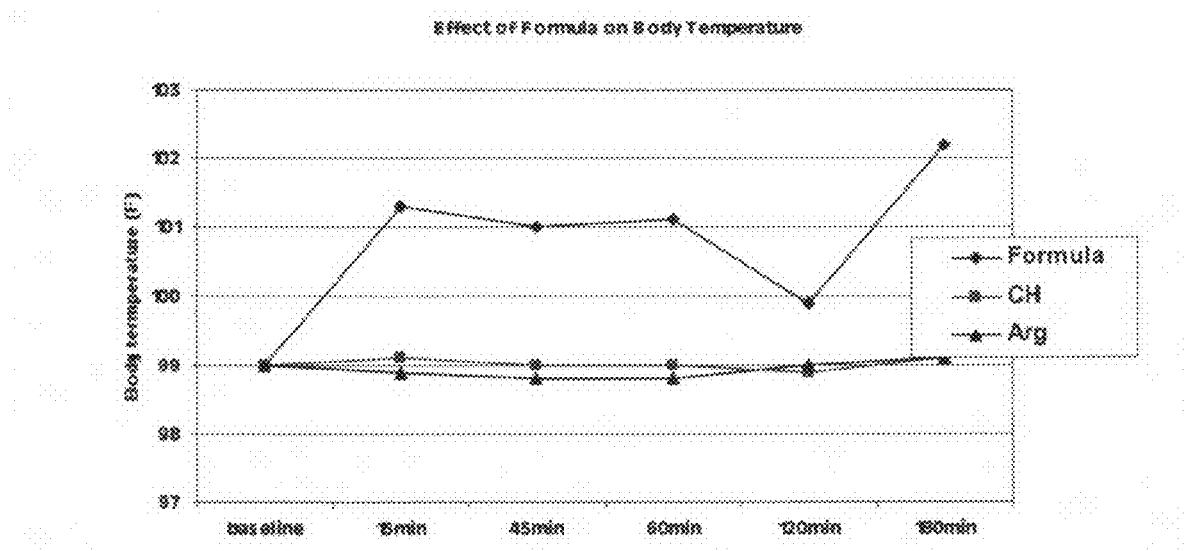
FIG. 3 illustrates a graph depicting the effect of formula on body temperature according to an embodiment of the present invention.

A 37-year-old female ingested the preparation designed to increase nitric oxide and acetylcholine in order to induce vasodilation (example 3). The preparation included choline, arginine, hawthorn berry, cocoa, dextrose, and cinnamon. A temperature probe designed to assess skin temperature measured vasodilation of the skin. The baseline skin temperature was 99 degrees Fahrenheit. Within fifteen minutes after ingestion of the capsules, the skin temperature increased to 101.3 degrees Fahrenheit and remained elevated for three hours. The next day arginine alone was given with no effect on skin temperature. The following day, choline alone was given with no effect on skin temperature. The preparation was given for two weeks when skin temperature was again measured. The skin temperature increased by two degrees and remained elevated for 60 minutes (FIG. 3).

EXAMPLE 8

A 54-year-old male took a preparation designed to increase nitric oxide, acetylcholine, and white blood cell release in order to ameliorate the effects of oral herpes simplex (cold sore) on the lip. The preparation included choline, arginine, hawthorn berry, cocoa, dextrose, and cinnamon, along with 100 mg of echinacea. At the time of initial symptoms of the oral lesion, he ingested four capsules and repeated the dose every four hours for 48 hours while awake. The lesion disappeared in 24 hours. Five other herpes simplex lesions of the lip were treated in three additional subjects; each of the oral lesions disappeared within 24 hours. This is in contradistinction to the known natural history of oral herpes simplex lesions that last 7 to 14 days.

EXAMPLE 9

A 54-year-old male took a preparation designed to increase nitric oxide, acetylcholine, and white blood cell release. The preparation included choline, arginine, hawthorn berry, cocoa, dextrose, and cinnamon, along with 100 mg of echinacea in order to ameliorate the symptoms of a common cold. At the onset of a sore throat and nasal congestion, he ingested four capsules. He repeated the dose every four hours for 48 hours. The symptoms were gone in 24 hours and the full expression of the cold did not evolve. Five other common colds in the early stages in 3 subjects were treated; the full expression of the cold did not evolve.

EXAMPLE 10

A 40-year-old male took a preparation designed to increase nitric oxide, acetylcholine, and white blood cell release. The preparation included choline, arginine, hawthorn berry, cocoa, dextrose, and cinnamon, along with 100 mg of echinacea in order to treat the symptoms of a fully expressed common cold. A fully expressed common cold with fever, nasal congestion, rhinorrhea, fatigue, and sore throat was treated with four capsules every four hours for 48 hours; the symptoms of the cold began to ameliorate within 8 hours and were gone within 48 hours.

EXAMPLE 11

Two females who had taken Fenfluramine and Phentermine to induce weight loss were tested for the presence of pulmonary hypertension, using color flow Doppler echocardiography. Both subjects had pulmonary hypertension at rest. The first subject had a systolic pulmonary artery pressure of 50 mm Hg, highly abnormal pulmonary artery pressures, indicating pulmonary hypertension. The second subject had a systolic pulmonary artery pressure of 55 mm Hg. Both subjects were given a preparation designed to induce nitric oxide production as given in example 3. The pulmonary artery pressures were re-measured 30 minutes after ingestion. In the first subject, the pulmonary artery pressure fell to 24 mm Hg, a normal pulmonary artery pressure. In the second subject, the pulmonary artery pressure fell to 17 mm Hg, also a normal pressure.

EXAMPLE 12

A 26-year-old Asian male with insomnia of many years duration took the preparation outlined in example 2 in order to increase serotonin and acetylcholine. The insomnia was characterized as failure to fall asleep for many hours after attempting to initiate sleep, and failure to sleep for more then one hour at a time. He took two capsules each night at bedtime. Within 2 days he began falling asleep within 10 minutes after ingesting the capsules and began to sleep for more then 4 hours. He maintained the improved sleep pattern for three months while taking the preparation each night. When he stopped taking the preparation, his insomnia retuned within 3 days. Upon resumption of the preparation, improvement of his sleep pattern returned. In an open label trial of 10 subjects with insomnia, 85% showed a similar response.

EXAMPLE 13

In a double blind trial of 26 patients with an autonomic nervous system dysfunction secondary to exposure to nitrogen tetroxide, the preparation described in example 1 was compared to both a placebo and to a choline preparation without hawthorn berry. The trial lasted six weeks to assess attenuation of the preparation. The HF-band increased towards normal in the group of subjects taking the preparation described in example 1. The HF band in the subjects in the placebo group did not change. The HF band in the choline alone group actually displayed further deterioration of autonomic nervous system function. The subjects in the choline alone group experienced an increase in heart rate, temperature dysregulation and cardiac arrhythmias. This example shows the avoidance of the attenuation response and the potential danger of administering neurotransmitter precursors without objective testing to assess response.

EXAMPLE 14

A useful formulation to produce norepinephrine, epinephrine, dopamine, histamine, acetylcholine and serotonin is tyrosine 50 mg choline 600 mg tryptophan in the form of predigested soy protein 220 mg, histidine 100 mg ginkgo biloba 120 mg, cocoa 200 mg and dextrose 200 mg. The formulation is designed to induce fat burning and suppress appetite. A preferred dose is three capsules twice daily. Other dosage schedules to induce other desirable effects of serotonin such as amelioration of depression can be used.

EXAMPLE 15

Figure 4:
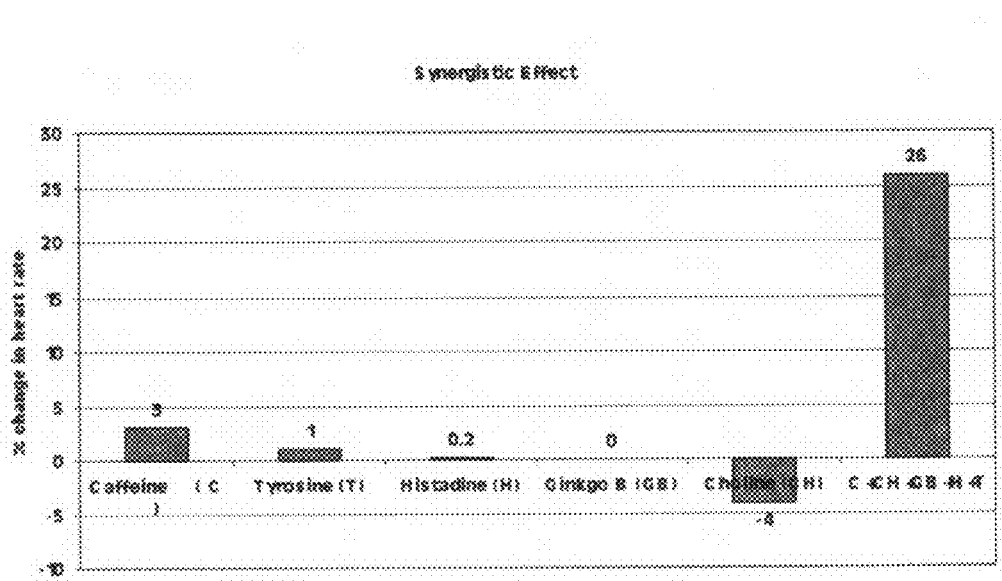
FIG. 4 illustrates a graph depicting the synergistic effect according to an embodiment of the present invention.

To test the components of example 14, a series of experiments were performed using a continuous heart rate recorder. In an individual on successive days, heart rate was recoded as RR intervals in msec. The individual sat quietly for 30 minutes as baseline. Then on day 1 the combination of caffeine, 150 mg, with tyrosine, 50 mg, histidine, 100 mg, Ginkgo Biloba, 120 mg, and choline 120 mg was given. The heart rate was defined as baseline taken just before ingestion and at 5 minutes, 10 minutes, 15 minutes, and 30 minutes. A percent change was calculated with the baseline as reference. On Day 2 caffeine alone was ingested using the same protocol. On day 3, tyrosine alone was ingested. On day 4, histidine was ingested. On day 5, ginkgo biloba was ingested. On day 6, choline was ingested. The results are listed in table 1 and FIG. 4.

TABLE 1

| Caffeine (C) | Tyrosine (T) | Histadine (H) | *Ginkgo B* (GB) | Choline (CH) | C + CH + GB + H + T |
|---|---|---|---|---|---|
| 3 | 1 | 0.2 | 0 | −4 | 26 |

The values in table are percent change in heart rate.

These data demonstrate the synergistic effect of the combination outlined in example 14.

EXAMPLE 15

Figure 5:
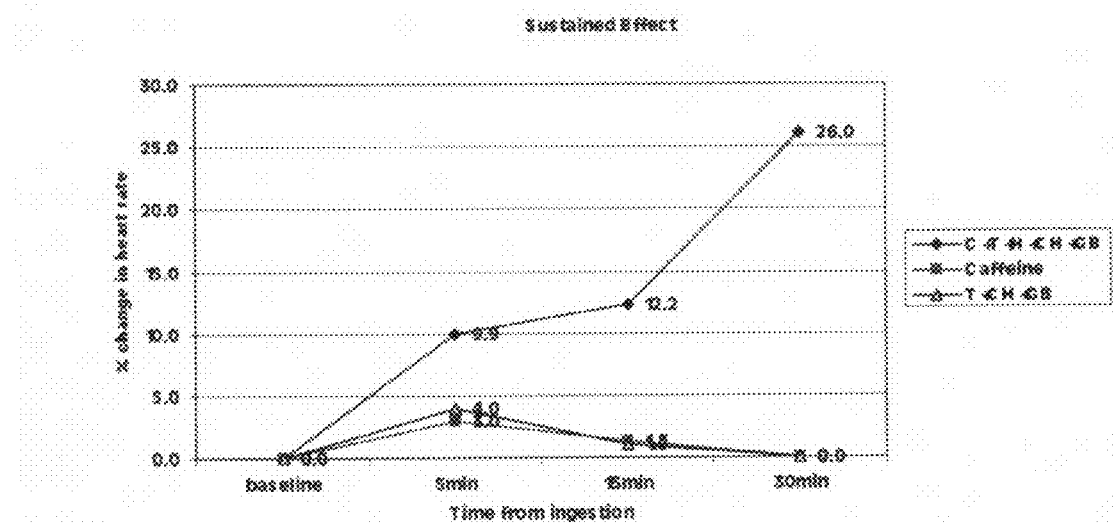
FIG. 5 illustrates a graph depicting the sustained effect according to an embodiment of the present invention.

In 6 individuals, heart rate experiments were performed to show the sustained effect of the combination of the five elements outlined in this invention. On day 1, the individuals had a continuous heart rate monitor connected. They sat quietly for 30 min to establish a baseline. They then on subsequent days ingested combination of the 5 elements described in this invention. The results are depicted in table 2 and FIG. 5.

TABLE 2

|  | baseline | 5 min | 15 min | 30 min |
|---|---|---|---|---|
| C + T + H + CH + GB | 0.0 | 9.9 | 12.2 | 26.0 |
| Caffeine | 0.0 | 3.0 | 1.3 | 0.0 |
| T + CH + GB | 0.0 | 4.0 | 1.0 | 0.0 |

Where C is caffeine 150 mg, T is tyrosine 50 mg, CH is choline 200 mg, and GB is *ginkgo biloba* 120 mg.

The synergistic combinations disclosed in this invention allow augmented and sustained activity of neurotransmitters. The effects of the neurotransmitter release are measured by physiological tests. The combination of elements produces the effects of neurotransmitter release without the attenuation usually associated with oral administration of neurotransmitters precursors.

The desired effects of neurotransmitter release induced by the combination of elements are not produced by the use of the individual components. Our invention allows improved parasympathetic nervous system function, improved cognitive function, reduced blood pressure, increased skin blood flow, improved initiation of sleep, improved maintenance of sleep, reduced QTc interval, reduced duration of herpes simplex oral lesions, and reduced duration of the symptoms of a common cold. Our invention allows these effects to occur over time without attenuation. Our invention requires the use of physiologic tests to assess responses. Previous attempts to use certain of the components in isolation were either ineffective, produced deleterious side effects or induced rapid attenuation.

Although the description above contains many specifications, these should not be construed as limiting the scope of the invention but as merely providing illustrations of some of the presently preferred embodiments of this invention. Various other embodiments and ramifications are possible within it's scope.

Thus the scope of the invention should be determined by the appended claims and their legal equivalents, rather than by the examples given.

What is claimed:

1. A method for enhancing epinephrine and norepinephrine neurotransmitter activity, comprising orally administering to a subject in need thereof a composition comprising:
    at least one first component selected from the group consisting of tryptophan and 5-hydroxytryptophan in the range of from about 1 mg to about 100 mg;
    at least one second component selected from the group consisting of glutamine, predigested protein, *Ginkgo biloba*, ginseng, cinnamon, nutmeg, and St. John's Wort in the range of from about 1 mg to about 200 mg;
    at least one third component selected from the group consisting of cocoa, caffeine, and theobromine in the range of from about 1 mg to about 200 mg;
    at least one fourth component selected from the group consisting of neuroexcitatory amino acids, glutamate, glutamic acid, and glutamine in the range of from about 1 mg to about 200 mg; and
    hawthorn berry as a fifth component in the range of from about 1 mg to about 200 mg,
    wherein the proportions of the five or more components are determined by testing said subject using a physiologic test selected from the group consisting of heart rate, 24 hour Electrocardiogram analysis, blood pressure, body temperature, skin temperature, and a neurotransmitter blood test.

2. The method for enhancing epinephrine and norepinephrine neurotransmitter activity of claim 1 wherein said oral administration is provided in a form selected from the group consisting of capsules, suspension caplets, chewable wafers, tablets, or powders.

3. A method for enhancing acetylcholine neurotransmitter activity, comprising orally administering to a subject in need thereof a composition comprising:
    at least one first component selected from the group consisting of choline and acetylcarnitine in the range of from about 20 mg to about 100 mg;
    at least one second component selected from the group consisting of tryptophan and 5-hydroxytryptophan in the range of from about 20 mg to about 100 mg;
    at least one third component selected from the group consisting of *Ginkgo biloba*, ginseng, cinnamon, nutmeg, and *Echinacea* in the range of from about 50 mg to about 100 mg;
    at least one fourth component selected from the group consisting of cocoa, caffeine, and theobromine in the range of from about 100 mg to about 200 mg;
    at least one fifth component selected from the group consisting of neuroexicitatory amino acids, glutamate, glutamic acid, and glutamine in the range of from about 20 mg to about 100 mg; and
    at least one sixth component selected from the group consisting of hawthorn berry and caffeine in the range of from about 20 mg to about 40 mg,
    wherein the proportions of the six or more components are determined by testing said subject using a physiologic test selected from the group consisting of heart rate, 24 hour Electrocardiogram analysis, blood pressure, body temperature, skin temperature, and a neurotransmitter blood test.

4. The method for enhancing acetylcholine neurotransmitter activity of claim 3 wherein said oral administration is provided in a form selected from the group consisting of capsules, suspension caplets, chewable wafers, tablets, or powders.

* * * * *